United States Patent
Friebe et al.

[11] Patent Number: 5,856,325
[45] Date of Patent: Jan. 5, 1999

[54] BENZOTRIAZINES, PHARMACEUTICAL COMPOSITIONS, AND METHODS OF USING SAME

[75] Inventors: Walter-Gunar Friebe, Mannheim; Werner Scheuer, Bad Tölz; Ulrich Tibes, Frankfurt, all of Germany

[73] Assignee: Boehringer Mannheim GmbH, Germany

[21] Appl. No.: 464,631

[22] PCT Filed: Dec. 15, 1993

[86] PCT No.: PCT/EP93/03542

§ 371 Date: Jun. 26, 1995

§ 102(e) Date: Jun. 26, 1995

[87] PCT Pub. No.: WO94/14781

PCT Pub. Date: Jul. 7, 1994

[30] Foreign Application Priority Data

Dec. 24, 1992 [DE] Germany .................. 42 44 009.2

[51] Int. Cl.[6] .................. C07D 253/10; A61K 31/53
[52] U.S. Cl. .................. 514/243; 544/183
[58] Field of Search .................. 514/243; 544/183

[56] References Cited

U.S. PATENT DOCUMENTS

| | | | |
|---|---|---|---|
| 2,489,351 | 11/1949 | Wolf et al. | 544/183 |
| 2,489,352 | 11/1949 | Wolf et al. | 544/183 |
| 2,489,353 | 11/1949 | Wolf et al. | 544/183 |
| 2,489,357 | 11/1949 | Wolf et al. | 544/183 |
| 2,489,359 | 11/1949 | Wolf et al. | 544/183 |
| 3,562,270 | 2/1971 | Wagner-Jauregg et al. | 544/183 |
| 3,681,334 | 8/1972 | Schmidt et al. | 544/183 |
| 4,067,981 | 1/1978 | Sasse et al. | 544/183 |
| 5,175,287 | 12/1992 | Lee et al. | 544/183 |

*Primary Examiner*—John M. Ford
*Attorney, Agent, or Firm*—Nikaido Marmelstein Murray & Oram, LLP

[57] ABSTRACT

Use of compounds of the formula I

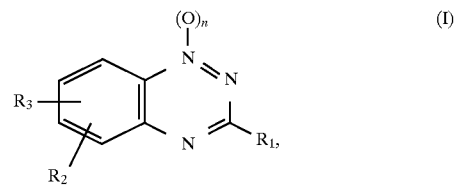

in which $R_1$ signifies an amino, $C_1$–$C_6$-alkylamino, di-$C_1$–$C_6$-alkylamino or a hydroxyl group, $R_2$ and $R_3$, which are the same or different, each hydrogen, halogen, $C_1$–$C_6$-alkyl, $C_1$–$C_6$-alkoxy, cyano, carboxyl, halogen-$C_1$–$C_6$-alkyl, cyano-$C_1$–$C_6$-alkyl, carboxy-$C_1$–$C_6$-alkyl, $C_1$–$C_6$-alkyl, hydroxyl, carboxy-$C_1$–$C_6$-alkoxy, $C_1$–$C_6$-alkoxycarbonyl-$C_1$–$C_6$-alkoxy or aminocarbonyl-$C_1$–$C_6$-alkoxy, $C_1$–$C_6$-alkylaminocarbonyl-$C_1$–$C_6$-alkoxy or di-$C_1$–$C_6$-alkylaminocarbonyl-$C_1$–$C_6$-alkoxy and n the number 0 or 1, their tautomers, as well as salts with non-toxic acids or bases, for the preparation of medicaments with $PLA_2$-inhibiting action, new compounds and process for their preparation.

10 Claims, No Drawings

BENZOTRIAZINES, PHARMACEUTICAL COMPOSITIONS, AND METHODS OF USING SAME

This is a National Stage Entry Application, filed under 35 U.S.C. 371, of PCT/EP93/03542, filed Dec. 15, 1993.

The subject of the present invention is the use of benzotriazines as $PLA_2$ inhibitors, new benzotriazine derivatives, process for their preparation and medicaments which contain these compounds.

The invention concerns the use of benzotriazine derivatives of the general formula I

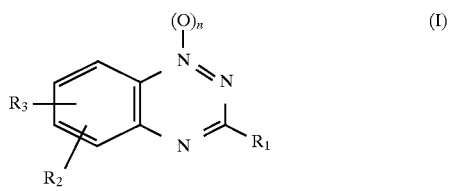

for the preparation of medicaments with $PLA_2$-inhibiting action, whereby $R_1$ signifies an amino, $C_1$–$C_6$-alkylamino, di-$C_1$–$C_6$-alkylamino or a hydroxyl group, $R_2$ and $R_2$, which are the same or different, each hydrogen, halogen, $C_1$–$C_6$-alkyl, $C_1$–$C_6$-alkoxy, cyano, carboxyl, halogen-$C_1$–$C_6$-alkyl, cyano-$C_1$–$C_6$-alkyl, carboxy-$C_1$–$C_6$-alkyl, hydroxyl, carboxy-$C_1$–$C_6$-alkoxy, $C_1$–$C_6$-alkoxycarbonyl-$C_1$–$C_6$-alkoxy or aminocarbonyl-$C_1$–$C_6$-alkoxy, $C_1$–$C_6$-alkylaminocarbonyl-$C_1$–$C_6$-alkoxy or di-$C_1$–$C_6$-alkylamino-carbonyl-$C_1$–$C_6$-alkoxy and n the number. 0 or 1, their tautomers, as well as salts with non-toxic acids or bases.

Compounds of the formula I are in part known. Thus, e.g. in J. Amer. Chem. Soc. 76, 3551 (1954), compounds of the formula I with $R_2$=Cl or H and $R_1$=OH or $NH_2$, $R_3$=H and n=O are described as anti-malarial agents. Further compounds with n=1 and $R_1$=$NH_2$ are known from J. Chem. Soc. (B) 1970. 911. In these documents, they are described as dyestuffs, radiosensitisers, bactericides, insecticides, acaricides, cytotoxic agents and anti-malarial agents. An anti-inflammatory action is not stated.

The compounds of the formula I display valuable pharmacological properties, especially they can inhibit the activity of phospholipases. Therefore, they are suitable for the treatment of acute and chronic, allergic, non-allergic and traumatic inflammatory diseases, such as for example rheumatic arthritis, osteoarthritis, ulcerative colitis, acute pancreatitis, contact dermatitis, inflammatory and allergic respirarory diseases, septic shock, allergic shock, serum disease, auto-immune diseases, graft-versus-host reactions, host-versus-graft diseases, ischaemic or thrombotic diseases, for example coronary infarct or cerebral infarct.

The "alkyl parts" in the aliphatic groups mentioned in the case of $R^2$ and $R^3$ can be straight-chained or branched. Preferred radicals are the methyl, ethyl, n-propyl, isopropyl, n-butyl, isobutyl, tert.-butyl, n-pentyl and 3-pentyl radical. As $C_1$–$C_6$-alkoxy group, in this sense there come into question, for example, the methoxy, ethoxy, propoxy or butoxy group.

Halogen atoms are especially fluorine, chlorine and bromine.

Apart from the compounds mentioned in the Examples, the subject of the invention are especially all substances which display all possible combinations of the substituents mentioned in the Examples.

The subject of the invention are also new compounds of the formula Ia

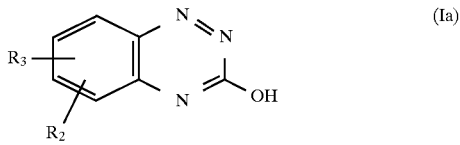

in which $R_2$ signifies $C_1$–$C_6$-alkyl, $C_1$–$C_6$-alkoxy, cyano, halogen-$C_1$–$C_6$-alkyl, cyano-$C_1$–$C_6$-alkyl, carboxy-$C_1$–$C_6$-alkyl, hydroxyl, carboxy-$C_1$–$C_6$-alkoxy, $C_1$–$C_6$-alkoxy-carbonyl-$C_1$–$C_6$-alkoxy, aminocarbonyl-$C_1$–$C_6$-alkoxy, $C_1$–$C_6$-alkylaminocarbonyl-$C_1$–$C_6$-alkoxy or di-$C_1$–$C_6$-alkylaminocanbonyl-$C_1$–$C_6$-alkoxy and $R_3$ hydrogen or $C_1$–$C_6$-alkyl, their tautomers, as well as salts with non-toxic acids or bases.

The compounds of the formula I and Ia, respectively, are especially suitable for the preparation of medicaments for the treatment of acute or chronic diseases, especially those diseases with inflammatory, immunological, allergic, non-allergic or traumatic genesis. Since phospholipase $A_2$ ($PLA_2$) is a key enzyme in the causation of these: diseases, such diseases are effecively treated by inhibition of this enzyme. Surprisingly, it has now been found that the compounds of the formula I or Ia, respectively, inhibit phospholipase $A_2$ and thus, on the basis of this new action profile, can be used in the treatment of diseases in which the inhibition of phospholipase $A_2$ is of clinical, pathological or symptomatic relevance., especially in the case of inflammatory diseases.

In the case of compounds of the formula I, $R^1$ preferably signifies an amino or hydroxyl group.

In the case of the compounds of the formula I or Ia, the substituents $R^2$ and $R^3$ can, independently of one another, stand in the 5-, 6-, 7- or 8-position of the benztriazole system. Preferably, there come into question derivatives monosubstituted on the phenyl ring ($R^3$=hydrogen and $R^2$ not hydrogen). In the case of disubstituted derivatives (neither $R^2$ nor $R^3$ hydrogen), the substituents $R^2$ and $R^3$ preferably stand in the 6- and 7-position of the benztriazole system.

Preferred radicals for $R^2$ are especially the following substituents: chlorine, methyl, ethyl, isopropyl, t-butyl, methoxy, 1,1-dimethylcyanomethyl, hydroxyl, carboxymethoxy. $R^3$ preferably signifies hydrogen or the methyl group.

The process according to the invention for the preparation of the compounds of the formula I or Ia, respectively, is characterised in that, in per se known way, one reacts a compound of the general formula II

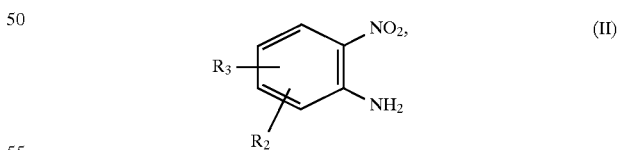

in which $R_2$ and $R_3$ have the above-mentioned meaning, with cyanamide and cyclises under basic conditions and subsequently converts the product obtained by reduction and subsequent diazotisation and hydrolysis into a compound of the formula I, in which $R_2$ and $R_3$ have the above-mentioned meaning, as well as possibly converts into a salt by neutralisation with non-toxic acids or bases.

The reaction of compounds of the formula II with cyanamide expediently takes place in aqueous medium with proton catalysis and warming, for example in conc. hydrochloric acid, the subsequent cyclisation in a basic medium with warming, for example in semiconc. caustic soda lye.

A reduction if desired to be carried out takes place expediently in a solvent, such as for example a lower alcohol or water or a mixture thereof, such as for example dil. ethanol, with a reducing agent, such as sodium dithionite. However, it can also be carried out in a solvent, such as a lower alcohol, with catalytically activated hydrogen with nickel catalysis or in acetic acid with iron powder or zinc.

A diazotisation if desired to be carried out expediently takes place with nitrous acid, prepared from alkali metal nitrites, such as e.g. sodium nitrite, in acids, such as e.g. acetic acid, hydrochloric acid or sulphuric acid, at temperatures between −20° C. and +30° C. For the hydrolysis, it can be left to stand in aqueous medium or, if desired, warmed.

As pharmacologically compatible salts, there come into question especially alkali metal, alkaline earth metal and ammonium salts, as well as possibly salts with non-toxic inorganic or organic salts, such as e.g. hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

One obtains the salts in the usual way, e.g. by neutralisation of the compounds of the formula I with the corresponding lyes or acids.

For the preparation of medicaments, the compounds of the general formula I are mixed in per se known manner with suitable pharmaceutical carrier substances, aroma, flavouring and colouring materials and formed, for example as tablets or dragees, or, with addition of appropriate adjuvants, suspended or dissolved in water or oil, such as e.g. olive oil.

The substances of the general formula I or Ia can be administered orally and parenterally in liquid or solid form. As injection medium, there is preferably used water which contains the stabilising agents, solubilising agents and/or buffers usual in the case of injection solutions. Such additives are e.g. tartrate or borate buffers, ethanol, dimethyl sulphoxide, complex formers (such as ethylenediaminetetraacetic acid), high molecular polymers (such as liquid polyethylene oxide) for viscosity regulation or polyethylene derivatives of sorbitol anhydrides.

Solid carrier materials are e.g. starch, lactose, mannitol, methyl cellulose, talc, highly dispersed silicic acid, high molecular polymers (such as polyethylene glycols).

Compositions suitable for oral administration can, if desired, contained flavouring and sweetening materials. For the external use, the substances I according to the invention can also be used in the form of powders and salves. For this purpose, they are mixed e.g. with powdered, physiologically compatible dilution agents or usual salve bases. The administered dose depends upon the age, the state of health and the Weight of the recipient, the extent of the disease, the nature of further treatments possibly carried out simultaneously, the frequency of the treatments and the nature of the desired action. Usually, the daily dose of the active compound amounts to 0.1 to 50 mg/kg of body weight. Normally, 0.5 to 4.0 and preferably 1.0 to 20 mg/kg/day in one or more applications per day are effective in order to obtain the desired results.

Apart from the substances mentioned in the Examples, the following compounds are preferred in the meaning of the present invention:

7-isoproipyl-12,4-benzotriazin-3-ol
7-t-butyl-1,2,4-benzotriazin-3-ol
6,7-dimethyl-1,2,4-benzotriazin-3-ol
7-hydroxy-1,2,4-benzotriazin-3-ol
6-chloro-1,2,4-benzotriazin-3-ol
7-chloro-1,2,4-benzotriazin-3-ol
7-methoxy-1,2,4-benzotriazin-3-ol
7-carboxymethoxy-1,2,4-benzotriazin-3-ol

EXAMPLE 1

1,2,4-Benzotriazine-3-amine 1-oxide

A mixture of 10 g 2-nitroaniline and 20 g cyanamide is heated for 5 min to 100° C., cooled, mixed with 25 ml conc. hydrochloric acid and carefully heated to 70° C. After subsidence of the vigorous reaction, one cools to room temp., adds dropwise thereto 50 ml semiconce. caustic soda lye, heats for 30 min to 100° C., cools, filters and washes the precipitate with hot glacial acetic acid. There remain 9.1 g of title compound (78% of theory) of the m.p. 272°–274° C.

EXAMPLE 2

In a manner analogous to that described in Example 1, one obtains:

| designation | yield (%) | melting point °C. (solvent) |
|---|---|---|
| a) 6-chloro-1,2,4-benzotriazine-3-amine 1-oxide from 5-chloro-2-nitroaniline | 58 | above 300 (glacial acetic acid) |
| b) 7-chloro-1,2,4-benzotriazine-3-amine 1-oxide from 4-chloro-2-nitroaniline | 81 | above 280 (glacial acetic acid) |
| c) 5-methyl-1,2,4-benzotriazine-3-amine 1-oxide from 3-methyl-6-nitroaniline | 72 | 266–268 (glacial acetic acid) |
| d) 6-methyl-1,2,4-benzotriazine-3-amine 1-oxide from 5-methyl-2-nitroaniline | 77 | 284–286 (glacial acetic acid) |
| e) 7-methyl-1,2,4-benzotriazine-3-amine 1-oxide from 4-methyl-2-nitroaniline | 98 | 276–278 (glacial acetic acid) |
| f) 8-methyl-1,2,4-benzotriazine-3-amine 1-oxide from 3-methyl-2-nitroaniline | 96 | 277-279 (glacial acetic acid) |
| g) 7-ethyl-1,2,4-benzotriazine-3-amine 1-oxide from 4-ethyl-2-nitroaniline | 94 | 225–227 (glacial acetic acid) |
| h) 7-isopropyl-1,2,4-benzo-triazine-3-amine 1-oxide from 4-isopropyl-2-nitro-aniline | 87 | 250–252 (glacial acetic acid) |
| i) 7-t-butyl-1,2,4-benzotriazine-3-amine-1-oxide from 4-t-butyl-2-nitroaniline | 77 | 143–145 (ethyl acetate) |
| j) 6,7-dimethyl-1,2,4-benzo-triazine-3-amine 1-oxide from 4,5-dimethyl-2-nitroaniline | 97 | above 270 (glacial acetic acid) |
| k) 5-methoxy-1,2,4-benzo-triazine-3-amine 1-oxide from 2-methoxy-6-nitro-aniline | 91 | above 270 (glacial acetic acid) |
| l) 7-methoxy-1,2,4-benzo-triazine-3-amine 1-oxide 4-methoxy-2-nitroaniline | 96 | 273–274 (glacial acetic acid) |
| m) 7-(1,1-dimethylcyano-methyl)-1,2,4-benzo-triazine 3-amine 1-oxide from 4-(1,1-dimethylcyano-methyl)-2-nitroaniline | 98 | 226–228 (water) |
| n) 7-hydroxy-1,2,4-benzo-triazine-3-amine 1-oxide from 4-hydroxy-2-nitro-aniline | 95 | above 270 (glacial acetic acid) |

EXAMPLE 3

1,2,4-Benzotriazine-3-amine

A mixture of 8.1 g (49 mmol) 1,2,4-benzotriazine-3-amine 1-oxide, 8.1 g sodium dithionite and 800 ml percent ethanol is heated under reflux for 1 h. One filters hot, evaporates the filtrate, washes the residue with water and dries. There remain 7.0 g 1,2,4-benzotriazine-3-amine (98% of theory) of the m.p. 208°–210° C.

EXAMPLE 4

In a manner analogous to that described in Example 3, one obtains:

| designation | yield (%) | melting point °C. (solvent) |
|---|---|---|
| a) 5-methyl-1,2,4-benzotriazine-3-amine from compound of Example 2c | 97 | 198–200 (water) |
| b) 6-methyl-1,2,4-benzotriazine-3-amine from compound of Example 2d | 95 | 238–240 (water) |
| c) 7-methyl-1,2,4-benzotriazine-3-amine from compound of Example 2e | 100 | 212–214 (water) |
| d) 8-methyl-1,2,4-benzotriazine-3-amine from compound of Example 2f | 86 | 260–262 (water) |
| e) 7-ethyl-1,2,4-benzotriazine-3-amine from compound of Example 2g | 59 | 164–166 (water) |
| f) 5-methoxy-1,2,4-benzotriazine-3-amine from compound of Example 2k | 94 | 230–232 (water) |

EXAMPLE 5

1,2,4-Benzotriazin-3-ol

To a solution of 2.0 g (14 mmol) 1,2,4-benzotriazine-3-amine in 30 ml water and 3 ml conc. sulphuric acid one adds dropwise at 10° C. a solution of 1 g sodium nitrite in 10 ml water. One stirs for 4 b at room temp., filters off the residue and dries. One obtains 1.1 g of title compound (55% of theory) of the m.p. 204–206° C.

EXAMPLE 6

In a manner analogous to that described in Example 5, one obtains:

| designation | yield (%) | melting point °C. (solvent) |
|---|---|---|
| a) 5-methyl-1,2,4-benzotriazin-3-ol from compound of Example 4a | 95 | 206–208 (water) |
| b) 6-methyl-1,2,4-benzotriazin-3-ol from compound of Example 4b | 73 | above 300 (ether) |
| c) 7-methyl-1,2,4-benzotriazin-3-ol from compound of Example 4c | 54 | 202–204) (ether) |
| d) 8-methyl-1,2,4-benzotriazin-3-ol from compound of Example 4d | 62 | 195–197 (ether) |
| e) 7-ethyl-1,2,4-benzotriazin-3-ol from compound of Example 4e | 39 | 180–182 (isohexane) |
| f) 5-methoxy-1,2,4-benzotriazin-3-ol from compound of Example 4f | 57 | 186–188 (ether) |

EXAMPLE 7

1,2,4-Benzotriazin-3-ol 1-oxide

To a solution of 7.5 g (46 mmol) 1,2,4-benzotriazine-3-amine 1-oxide (Chem. Ber. 46, 3522 (1913) in 75 ml water and 27 ml conc. sulphuric acid one adds dropwise at room temp. a solution of 13.3 g sodium nitrite in 25 ml water. One leaves to stand overnight, filters, takes up in soda solution, washes with ether, acidifies the aqueous phase, filters and recrystallises from glacial acetic acid. One isolates 4.7 g of title compound (63% of theory) of the m.p. 238–239° C.

EXAMPLE 8

In a manner analogous to that described in Example 7, one obtains:

| designation | yield (%) | melting point °C. (solvent) |
|---|---|---|
| a) 6-chloro-1,2,4-benzotriazin-3-ol 1-oxide from compound of Example 2a | 87 | 209–211 (water) |
| b) 7-chloro-1,2,4-benzotriazin-3-ol 1-oxide from compound of Example 2b | 62 | 241–243 (water) |
| c) 5-methyl-1,2,4-benzotriazin-3-ol 1-oxide from compound of Example 2c | 51 | 235–237 (water) |
| d) 6-methyl-1,2,4-benzotriazin-3-ol 1-oxide from compound of Example 2d | 77 | 238–240 (water) |
| e) 7-methyl-1,2,4-benzotriazin-3-ol 1-oxide from compound of Example 2e | 64 | 242–244 (water) |
| f) 8-methyl-1,2,4-benzotriazin-3-ol 1-oxide from compound of Example 2f | 65 | 236–238 (water) |
| g) 7-ethyl-1,2,4-benzotriazin-3-ol 1-oxide from compound of Example 2g | 33 | 184–186 (isopropanol) |
| h) 7-isopropyl-1,2,4-benzotriazin-3-ol 1-oxide from compound of Example 2h | 47 | 186–188 (isopropanol) |
| i) 7-t-butyl-1,2,4-benzotriazin-3-ol 1-oxide from compound of Example 2i | 24 | 210–212 (ether) |
| j) 6,7-dimethyl-1,2,4-benzotriazin-3-ol 1-oxide from compound of Example 2j | 52 | 230–232 (ethyl acetate) |
| k) 5-methoxy-1,2,4-benzotriazin-3-ol 1-oxide from compound of Example 2k | 42 | 241–243 (ethyl acetate) |
| l) 7-methoxy-1,2,4-benzotriazin-3-ol 1-oxide from compound of Example 2l | 84 | 242–244 (water) |
| m) 7-(1,1-dimethylcyanomethyl)-1,2,4-benzotriazin-3-ol 1-oxide from compound of Example 2m | 75 | 216–218 (water) |
| n) 7-hydroxy-1,2,4-benzotriazin-3-ol 1-oxide from compound of Example 2n | 57 | 264–265 (ether) |

EXAMPLE 9

7-(1,1-Dimethylcyanomethyl)-1,2,4-benzotriazin-3-ol

A solution of 1.5 g (6.5 mmol) of compound of Example 8m in 30 ml glacial acetic acid is mixed at 85° C. within 30 min with 1.8 g iron powder. One filters off with suction hot, after-washes with hot glacial acetic acid, evaporates the filtrate and chromatographs on silica gel. After elution with ethyl acetate/methanol 3:1 and trituration with ether, there remain 0.8 g of title compound (57% of theory) of the m.p. 183°–185° C.

EXAMPLE 10

Inhibition of the PLA$_2$ activity a) Inhibition of the human recombinant type II PLA$_2$) (=synovial PLA$_2$)

As typical respresentative of A PLA$_2$, there was selected for the testing the synovial PLA$_2$ (dissertation of Rainer Müller, 1993; University of Regensburg).

As representative of the compounds I or Ia, respectively, there was investigated in more detail the compound from Example 1. In the following Table, there is given dosage-dependent the percentage in vitro inhibition of PLA$_2$.

| compound from Example | PLA$_2$ inhibition [%] |
|---|---|
| 1  100 μg/ml | 99 |
| 1   10 μg/ml | 60 |
| 1    1 μg/ml | 43 | b) Inhibition of the collagen-induced arachidonic acid (AA) liberation from human thrombocytes As further indicator of a PLA$_2$ inhibition, there is valid an inhibition of the AA liberation from thrombocytes. For this purpose, the thrombocytes are equilibrated with $^3$H-AA. This added radioactive arachidonic acid incorporates into membrane phospholipids. Subsequently, the thrombocytary PLA$_2$ is activated via the collagen receptor and $^3$H-AA thus again liberated from the membrane phospholipids into the medium where it can be measured.

In table 1 is shown that the representative selected compound of example 1 inhibits dosage-dependent the collagen-induced AA liberation by up to 91%.

| compound of Example | inhibition of the AA liberation [%] |
|---|---|
| 1  100 μg/ml | 91 |
| 1   10 μg/ml | 29 |

We claim:

1. A method of inhibiting PLA$_2$ in a mammal in need of such inhibition comprising administering to said mammal a PLA$_2$ inhibiting effective amount of a compound of formula I

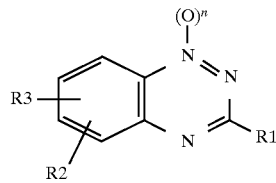

wherein

R$_1$ is hydroxyl,

R$_2$ and R$_3$, which are the same or different, are selected from the group consisting of hydrogen, chloro, C$_1$–C$_6$-alkyl, C$_1$–C$_6$-alkoxy, cyano-C$_1$–C$_6$-alkyl, and hydroxyl, and n is the number 0 or 1, their tautomers, and salts with non-toxic acids or bases.

2. The method of claim 1, wherein R$_2$ in 7- position is selected from the group consisting of hydrogen, chloro, C$_1$–C$_6$-alkyl, C$_1$–C$_6$-alkoxy, cyano- C$_1$-C$_6$-alkyl and a hydroxyl group.

3. The method of claim 1, wherein R$_3$ is selected from the group consisting of hydrogen and a C$_1$–C$_6$-alkyl group.

4. A compound of the formula Ia

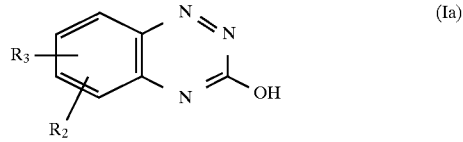

wherein

R$_2$ is in 7- position and is selected from the group consisting of hydrogen, C$_1$–C$_6$-alkyl, C$_1$–C$_6$- alkoxy, cyano-C$_1$–C$_6$-alkyl, and hydroxyl;

R$_3$ is a hydrogen or C$_1$–C$_6$-alkyl, wherein when R$_2$ is hydrogen, R$_3$ is a C$_1$–C$_6$-alkyl; and n is the number 0 or 1.

5. The compound of claim 4, wherein R$_2$ is CH$_3$, R$_3$ is hydrogen and n is the number 0 or 1.

6. A pharmaceutical composition comprising a compound of claim 4 and a pharmaceutically acceptable carrier or adjuvant.

7. A pharmaceutical composition comprising a compound of claim 5 and a pharmaceutically acceptable carrier or adjuvant.

8. A method for reducing inflammation by inhibiting PLA$_2$ in a mammal in need of such inhibition comprising administering to said mammal an inflammation reducing effective amount of a compound of formula I

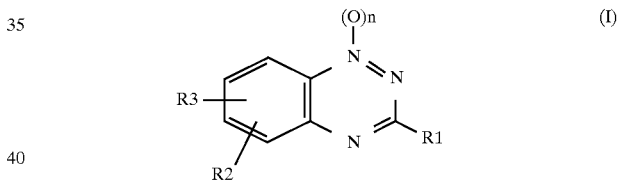

wherein

R$_1$ is hydroxyl,

R$_2$ and R$_3$, which are the same or different, are selected from the group consisting of hydrogen, chloro, C$_1$–C$_6$-alkyl, C$_1$–C$_6$-alkoxy, cyano-C$_1$–C$_6$-alkyl, and hydroxyl, and n is the number 0 or 1, their tautomers, and salts with non-toxic acids or bases.

9. The method of claim 8, wherein R$_2$ in 7- position is selected from the group consisting of hydrogen, chloro, C$_1$–C$_6$-alkyl, C$_1$–C$_6$-alkoxy, cyano- C$_1$–C$_6$-alkyl and a hydroxyl group.

10. The method of claim 8, wherein R$_3$ is hydrogen or C$_1$–C$_6$-alkyl group.

* * * * *